(12) United States Patent
Duan et al.

(10) Patent No.: US 11,191,426 B2
(45) Date of Patent: Dec. 7, 2021

(54) SYSTEM FOR CAPSULE ENDOSCOPE HAVING A DIAGNOSTIC IMAGING MEANS AND METHOD OF USING THE SAME

(71) Applicant: ANKON MEDICAL TECHNOLOGIES (SHANGHAI), LTD, Shanghai (CN)

(72) Inventors: Xiaodong Duan, Pleasanton, CA (US); Xinhong Wang, SanDiego, CA (US); Guohua Xiao, Plano, TX (US)

(73) Assignee: ANKON MEDICAL TECHNOLOGIES (SHANGHAI) CO., LTD., Shanghai (CN)

(*) Notice: Subject to any disclaimer, the term of this patent is extended or adjusted under 35 U.S.C. 154(b) by 893 days.

(21) Appl. No.: 15/922,920

(22) Filed: Mar. 16, 2018

(65) Prior Publication Data

US 2019/0282074 A1  Sep. 19, 2019

(51) Int. Cl.
*A61B 1/00*  (2006.01)
*A61B 1/04*  (2006.01)
*A61B 1/06*  (2006.01)
*A61B 5/06*  (2006.01)

(52) U.S. Cl.
CPC .......... *A61B 1/041* (2013.01); *A61B 1/00158* (2013.01); *A61B 1/0638* (2013.01); *A61B 1/0684* (2013.01); *A61B 5/062* (2013.01); *A61B 5/067* (2013.01)

(58) Field of Classification Search
CPC ............................. A61B 1/041; A61B 1/00158
See application file for complete search history.

(56) References Cited

U.S. PATENT DOCUMENTS

| | | | |
|---|---|---|---|
| 2009/0225157 A1 | 9/2009 | Orihara | |
| 2015/0018615 A1* | 1/2015 | Duan | A61B 1/00149 600/109 |
| 2015/0380140 A1* | 12/2015 | Duan | A61B 1/041 600/109 |
| 2016/0338578 A1* | 11/2016 | Tearney | A61B 1/00128 |

* cited by examiner

*Primary Examiner* — Alexandra L Newton
*Assistant Examiner* — Rynae Boler
(74) *Attorney, Agent, or Firm* — Treasure IP Group, LLC

(57) ABSTRACT

The present invention discloses an ingestible endoscopy capsule including a permanent magnetic dipole, and an external positioning and orientation system to position and/or orientate the capsule in a target area including at least one magnet for positioning and/or orientating the endoscopy capsule within a patient, and one diagnostic imaging means.

18 Claims, 18 Drawing Sheets

View of front end

Capsule 100

View from the side

View of the rear end

Capsule can be moved either forward or backward while being suspended horizontally Capsule can scan the surface above or below it while being suspended horizontally Figure 10: Capsule can be moved either forward or backward while being suspended vertically Capsule can scan the surface above or below it while being suspended vertically Capsule can scroll and scan the surface continuously while moving forward in a linear manner

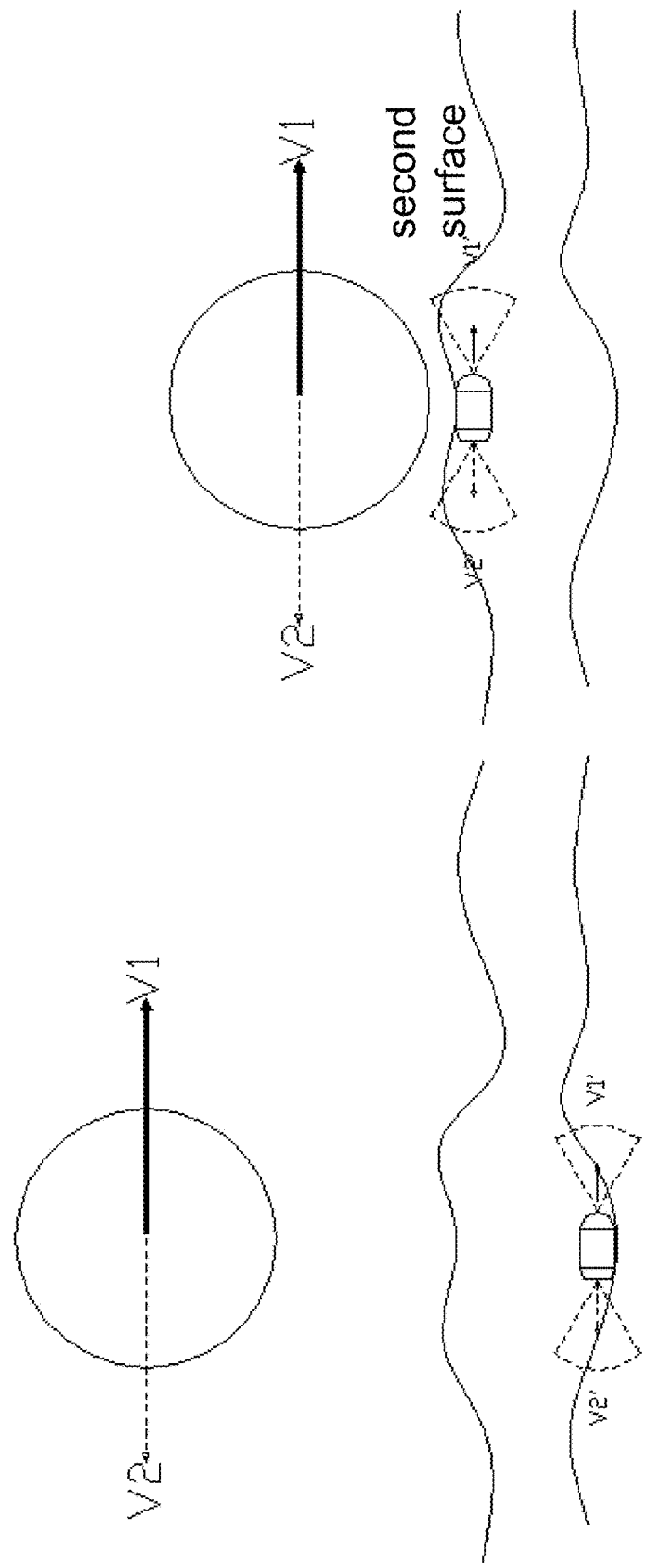

Capsule can scan the top surface while being anchored on the bottom surface

Capsule can scan the bottom surface while being anchored on the top surface

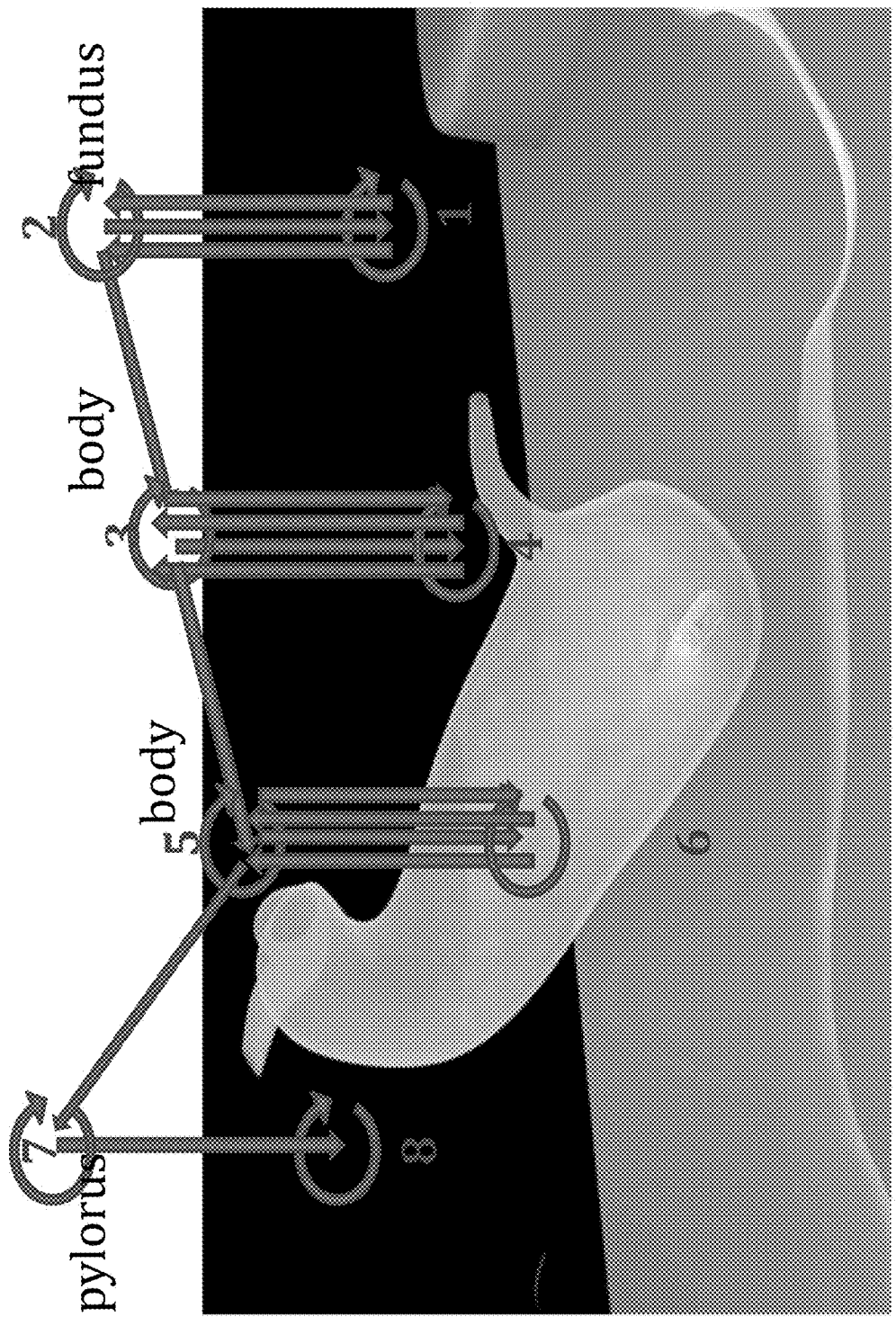

SYSTEM FOR CAPSULE ENDOSCOPE HAVING A DIAGNOSTIC IMAGING MEANS AND METHOD OF USING THE SAME

CROSS REFERENCE TO RELATED APPLICATIONS

None.

TECHNICAL FIELD

The invention relates to a medical apparatus/system and methods for performing capsule endoscopy and optical biopsy, specifically refers to a system and method to navigate magnetic capsule endoscope in a human GI track to a target location for performing video endoscopy imaging and Oblique Back Illumination Microscopy (OBM) to diagnose various disease conditions, especially for the early stage cancer in digest channel.

BACKGROUND OF THE INVENTION

Capsule endoscope is a miniaturized camera placed inside a capsule-shaped housing. When a patient swallows such a camera pill, the capsule endoscope travels along the patient's gastrointestinal tract and takes a series of pictures of the interior of the patient gastrointestinal tract. While the capsule endoscope passing through the patient's digestive system, the images taken would be simultaneously transmitted outside of the patient's body to a receiver, and then doctors use the image data for real-time medical examinations.

Capsule endoscopy not only has been demonstrated to be very successful in examining patience's interior, but shows clear advantage over traditional endoscope techniques when it comes to examining a patient's small intestine, where the areas or portions of the gastrointestinal tract are not readily accessible by traditional standard endoscopy techniques.

However, studies have shown that the images taken been could only been used as a screening tool. In order to make the capsule endoscope more useful, there is a need to add more optical detection components to the capsule endoscope so that the capsule endoscope can be used as a more accurate diagnostic technique.

Up to today, the prevalent way to get a more accurate diagnostic for an area of interest in a clinical environment is to perform a biopsy. Generally, a biopsy involves cutting a part of an tissue out from the area of interest, using a device to observe the tissue under high-resolution microscopy, and making an assessment based on morphological considerations. Because biopsy 1) only provides a sparse sampling which is not necessarily be fully representative of the region of interest; and
2) patient always has concerns about the risk of infection relating to tissue biopsies;
therefore, there is a need to reduce the labor/procedure with the potential risk of the biopsy. Since biopsy assessment is still a morphological consideration based on microscopy, the integration of the biopsy morphological detection techniques onto the a capsule endoscope can potentially offer "biopsy" in an entire region of interest, eliminate the sampling the produce and reduce patient discomfort and risks of infection and other possible complications.

SUMMARY OF THE INVENTION

The present invention discloses an endoscopic imaging apparatus comprising a diagnostic imaging means.

The present invention discloses an ingestible endoscopy capsule including a permanent magnetic dipole, and an external positioning and orientation system to position and/or orientate the capsule in a target area including at least one magnet for positioning and/or orientating the endoscopy capsule within a patient, and one diagnostic imaging means.

The present invention discloses an endoscopic imaging apparatus comprising a first multiple LEDs light source for photography or video and a second and third light LED source for diagnostic imaging.

BRIEF DESCRIPTION OF THE DRAWINGS

FIG. 14a shows a schematic illustration of an exemplary capsule endoscope in a target area, wherein the capsule endoscope of FIG. 1 can move along a first surface of the target area and scan the first surface;

FIG. 14b shows a schematic illustration of an exemplary capsule endoscope in a target area, wherein the capsule endoscope of FIG. 1 can move along a second surface of the target area;

FIG. 21 provides a schematic illustrates of an examination process.

DETAILED DESCRIPTION OF THE PREFERRED EMBODIMENTS

Figure 3:
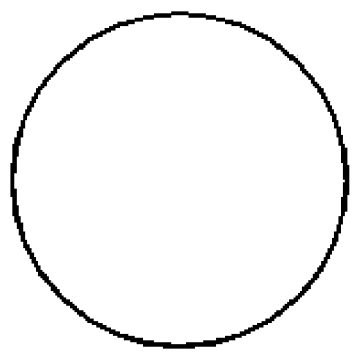
FIG. 3 shows a front end view of an exemplary capsule endoscope of FIG. 1.

Additional embodiments and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The capsule in the present invention is an endoscopic imaging apparatus. The capsule endoscope imaging apparatus comprises an ingestible endoscopy capsule including a permanent magnetic dipole, and an external positioning and orientation system to position and/or orientate the capsule in a target area including at least one magnet for positioning and/or orientating the endoscopy capsule within a patient, and one diagnostic imaging means.

The capsule endoscope disclosed herein, have two cameras. A first camera is a photographic camera, which is meant to scan the surface of the interior of the target area and sent image data outside of the patient body as the capsule travels through the gastrointestinal tract of the patient. A second camera is a diagnostic imaging means, which is aimed to perform optical biopsy in the target area, when a local diseased area is identified. The second camera has at least two illumination source which can illuminate the target area using differential wavelength. In one embodiment, the second camera is a OBM (OBLIQUE BACK ILLUMINATION MICROSCOPY). In one embodiment of the present invention, the diagnostic imaging means performs transverse imaging.

In another embodiment of the present invention, the diagnostic imaging means performs cross-sectional imaging.

In one example of the present invention, the diagnostic imaging means performs an imaging depth of 0.1-1 mm below one the surface of the target area.

In another example of the present invention, the diagnostic imaging means has an imaging depth resolution of 5 µm below one surface of the target area.

In the above still another example of the present invention, the diagnostic imaging means has an imaging lateral resolution of 1 µm.

The capsule endoscope comprises a permanent magnetic dipole. The permanent magnetic dipole can interact with the external magnetic field to move and orientate the capsule. In one embodiment of the present invention, the permanent magnetic dipole has a direction parallel to the length of the capsule. In one embodiment of the present invention, the capsule is cylindrical shape and having one hemi-sphere end. The cylindrical portion of the capsule endoscope has a length and a diameter. In one embodiment of the present invention, the capsule endoscope has a length less than 30 mm. In one embodiment of the present invention, the capsule has a diameter less than 10 mm. The capsule endoscope disclosed in the present invention, in one example, has a weight more than 3 g. In another example, the capsule endoscope has a weight less than 10 g. In another example, the capsule endoscope has a weight less than 8 g. In another example, the capsule endoscope has a weight less than 6 g. In another example, the capsule endoscope has a weight less than 5 g.

The capsule endoscope comprises a permanent magnetic dipole. The permanent magnetic dipole has a magnetic dipole direction along the length of the capsule endoscope. The capsule endoscope further has a weight center, which is the center of gravity in the capsule endoscope. The permanent magnetic dipole has a magnetic center. In order to offer easy operation of the capsule endoscope, in one example, the distance between the magnetic center and weight center is less than 2 mm. In another example, the length of the capsule endoscope is less than 12 mm.

Capsule endoscope in the present invention, is cylindrical shaped and having one semi-sphere end and one flat end. The capsule has a length and diameter. Length is the distance between the spherical ends, along the cylindrical direction. Preferably, the semi-sphere end consists of the video camera optical setup, the flat end consist of the microscopy for the optical biopsy. The capsule endoscope has a front end and a rear end, wherein the front end is ahead of the rear end in the movement direction. In one embodiment, the front end of the capsule endoscope is the end where the first camera is located. In one embodiment of the present invention, the first and second cameras are located at the different ends of the capsule endoscope. In another embodiment of the present invention, the first and second cameras are located at the same end of the capsule endoscope.

The capsules endoscope disclosed herein, can be either tethered or wireless. In one embodiment, the second camera is an OBM (OBLIQUE BACK ILLUMINATION MICROSCOPY) and the capsule is a wireless capsule. In another embodiment, and the capsule is a tethered capsule.

The capsules endoscope, in accordance with the present invention, has a weight greater than 3 g, and density greater than 1. In one embodiment of the present invention, the capsule can be suspended at the liquid and gas interface within the target area. In another embodiment of the present invention, the capsule can be floated immersed in the liquid while taking the pictures or performing an optical biopsy.

The capsules endoscope, in accordance with the present invention, may optionally further comprise surface abrasion structures to enhance friction between capsule endoscope and interior wall of the target area. Said surface abrasion structures may further help the capsule to be anchored at the specific location or disposed in the specific orientation. Said abrasion structures include any type of rings and protrusions. In one embodiment of the present invention, the capsule can be placed close to either top wall or the bottom wall of the target area, where in the longitude direction of the at the liquid and gas interface within the target area. In another embodiment of the present invention, the capsule can be floated or immersed in the liquid while taking the pictures or performing an optical biopsy.

In the scope of the present invention, in some examples, suspended horizontally means when a test subject lies down on a surface, and said surface is placed horizontally to the ground level, then the capsule is suspended parallel to the ground level. In the scope of the present invention, in some examples, suspended horizontally means when the capsule endoscope is placed in a target area, the target area has an interior wall which has a flat surface, and the capsule is either suspended by liquid or supported by the surface abrasion structures thereon, to be in parallel to at least one interior wall of target area. Further, if the interior area does not have a surface which is flat, for example, when the capsule endoscope examines the interior of a stomach, the capsule to be placed horizontally means, the length of the capsule is parallel to the tangent of the surface of a curved interior wall. In the scope of the present invention, in some examples, suspended vertically means when a test subject lies down on a surface, and said surface is placed horizontally to the ground level, then the capsule is suspended vertically to the ground level. In the scope of the present invention, in some examples, the capsule is supported vertically means when the capsule endoscope is placed in a target area, the target area has an interior wall which has a flat surface, and the capsule is supported by the surface abrasion structures thereon and perpendicular to the surface of the interior wall. In some examples, the capsule is supported vertically means when the capsule endoscope is placed in a target area, the target area has an interior wall which has a curved surface, and the capsule is supported by the surface abrasion structures thereon and perpendicular to the tangent of the curved surface of the interior wall. In some examples, the capsule is suspended vertically means when the capsule endoscope is placed in a target area having a liquid, the capsule is suspended at the liquid/gas interface vertically means the length direction of the capsule and liquid/gas interface form an angle around 90 degrees.

Figure 2:
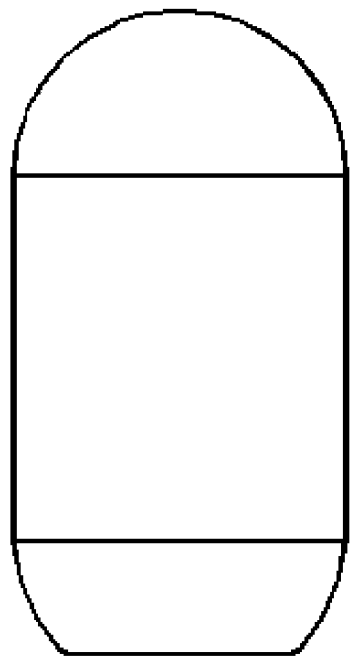
FIG. 2 shows a longitude or side view of an exemplary capsule endoscope of FIG. 1.
Figure 1:
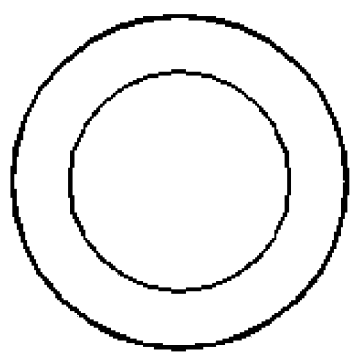
FIG. 1 shows a rear end view of an exemplary capsule endoscope according to one aspect of the present invention.
Figure 5:
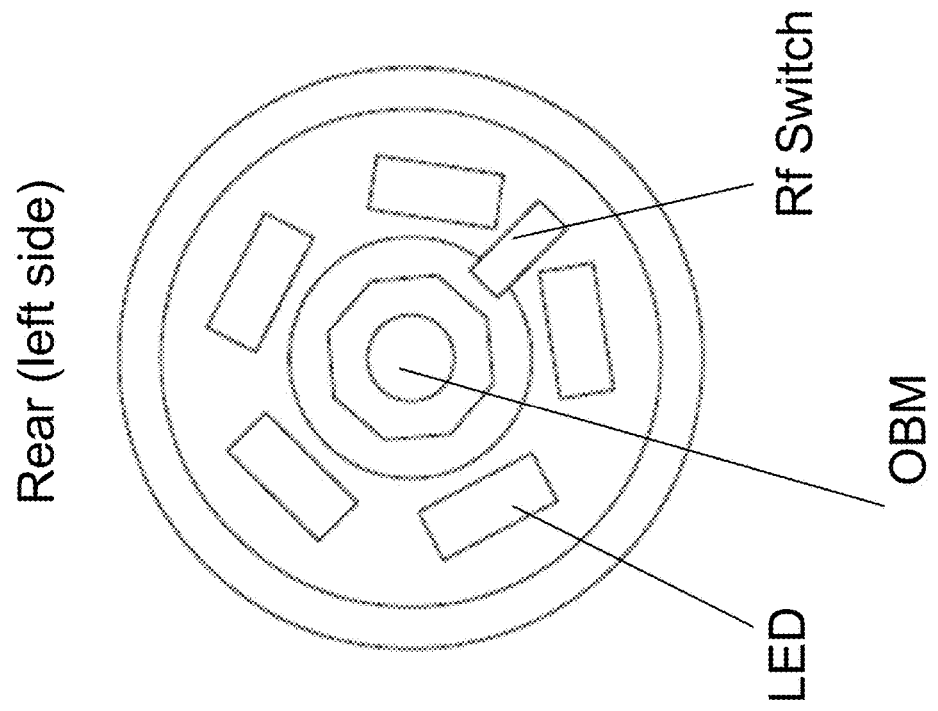
FIG. 5 shows a second cross-sectional view of the exemplary capsule endoscope of FIG. 1, viewing from the left/rear end of the capsule.
Figure 4:
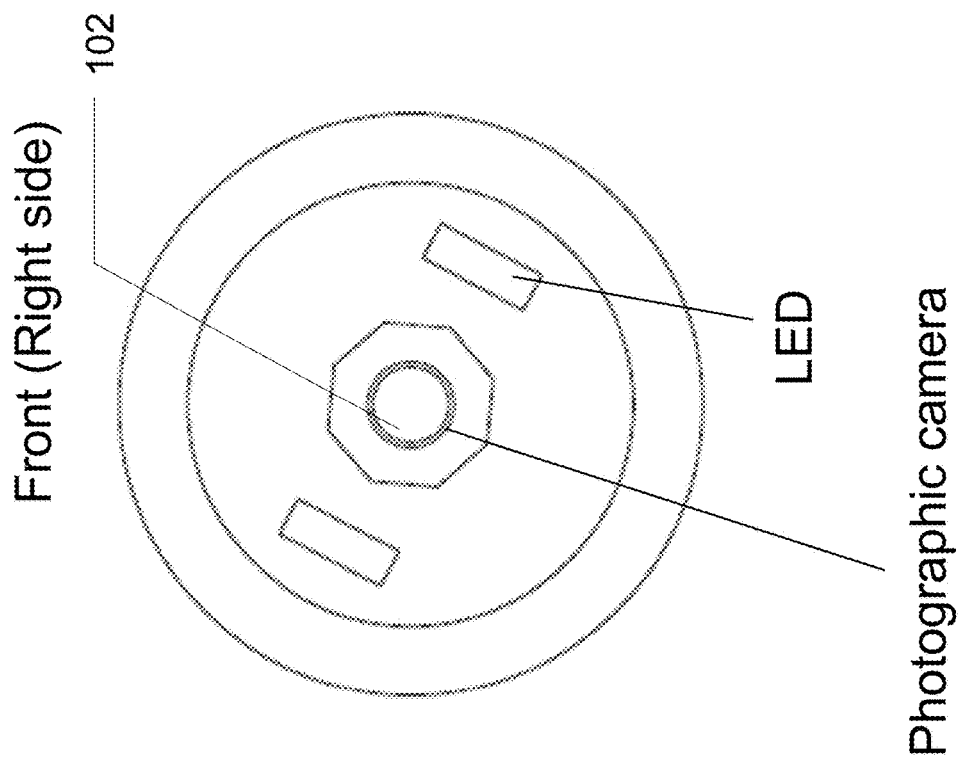
FIG. 4 shows a first cross-sectional view of the exemplary capsule endoscope of FIG. 1, viewing from the right/front end.

Referring to FIGS. 1-3, one exemplar embodiment of the capsule endoscope is illustrated. The capsule endoscope is substantially in a cylindrical shape having one semi-spherical end and one truncated semi-spherical end, wherein the semi-spherical end is the front end of the capsule endoscope and the truncated semi-spherical end is rear end of the capsule. FIGS. 4 and 5 show the cross sectional views of the front and rear ends of the capsule endoscope. The front end cross sectional view (FIG. 4) shows an exemplar illustration of the front end, which comprises a lens of a photographic camera and more than one LEDs. The LEDs (104) surround the photographic camera lens 102, preferably to be placed symmetrically around the photographic camera, so that the area needs to be illuminated can be lighted up more homogeneously. FIG. 5 illustrate an exemplar rear end structure of the capsule endoscope, wherein the one OBM (OBLIQUE BACK ILLUMINATION MICROSCOPY) camera is placed in the center of the circle in the cross sectional view, and is surrounded by multiple LEDs, in between of the two LEDs, there is a switch operated by IR signal. The IR switch is used to turn on the capsule endoscopy before examination.

Figure 6:
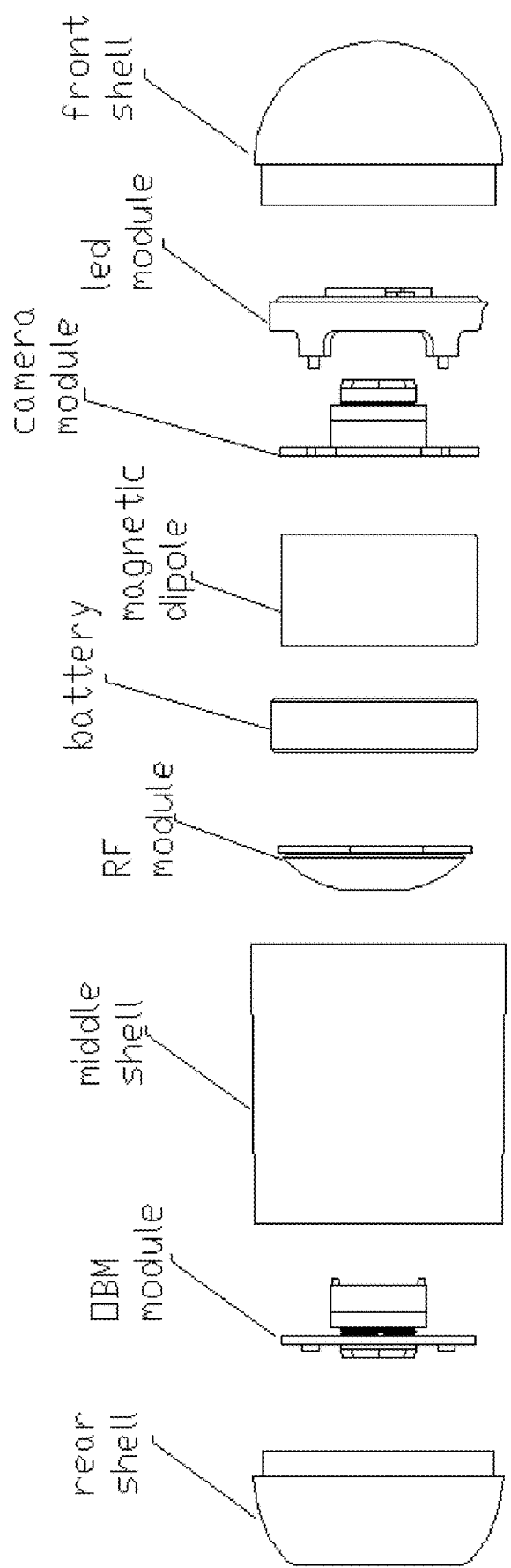
FIG. 6 shows a third cross-sectional view of the exemplary capsule endoscope of FIG. 1, viewing from the side along its length.
Figure 7:
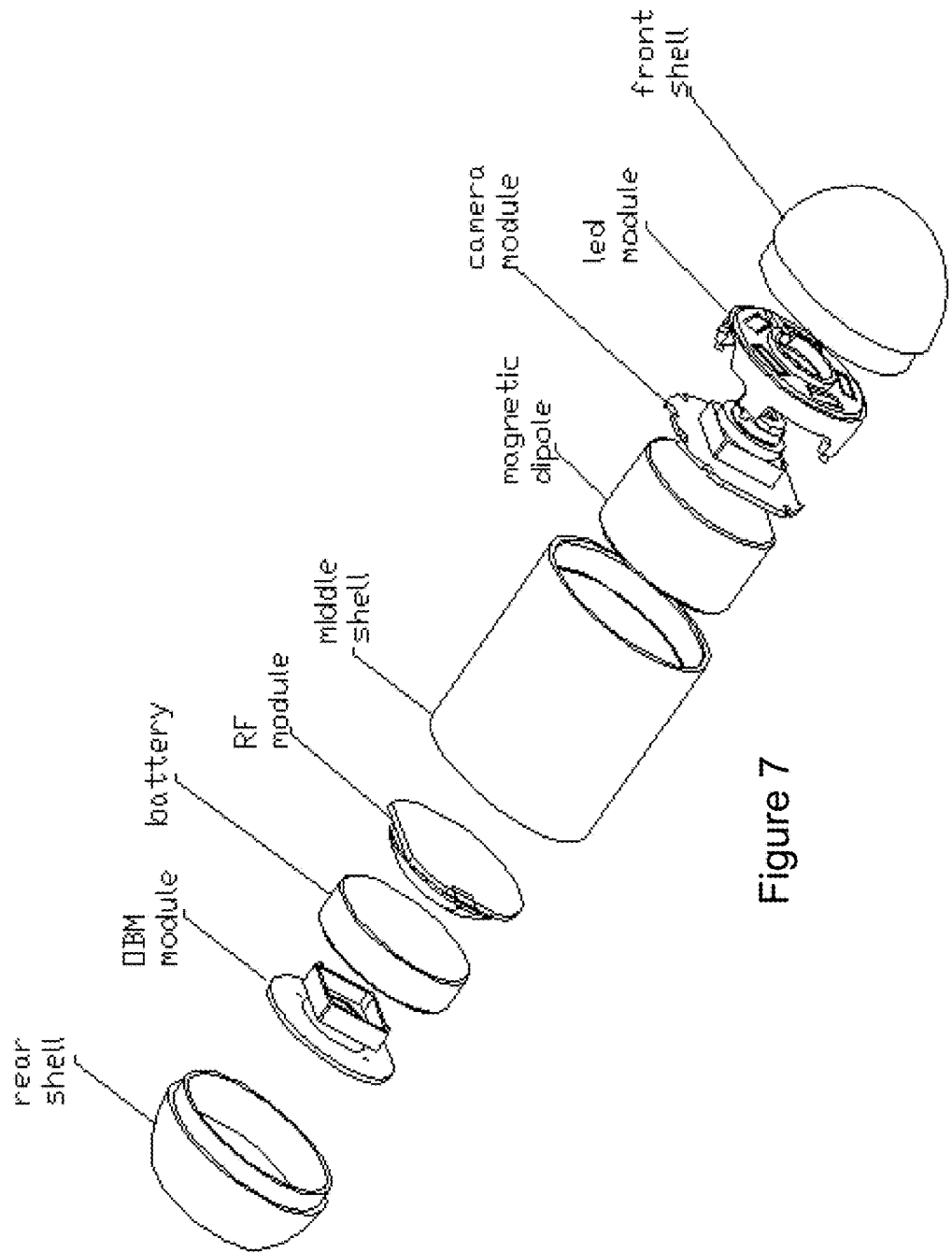
FIG. 7 shows an explored perspective view of the exemplary capsule endoscope of FIG. 1.

Exemplary structural components of the capsule endoscope in accordance with the present invention are schematically illustrated in FIG. 6. The capsule endoscope comprises a OBM module, situated in a rear shell, a RF module, a battery and magnetic dipole, enclosed in a middle shell and a photographic camera module coupled with a LED module, disposed in a front shell. In the capsule endoscope, the rear shell, middle shell and front shell have interlock mechanisms so that the middle shell can receive the rear shell and front shell and securely lock them in place. In one example, the interlock mechanisms are male/female joints. In one instance, the rear shell and front shell both have male joints, and both ends of the middle shell have female joints.

Referring to FIGS. 2, 3, 6 and 7, the front shell is substantially semi-sphere dome shaped. Because the front shell moves first as the capsule endoscope navigates through the gastrointestinal tract of a patient, the dome shaped front shell provides unique smooth and curved surface to help reduce friction, or even open up wrinkles of the walls of the gastrointestinal tract, while providing very minimal discomfort to the patient. Further the front shell is made of transparent materials. Further the front shell is made of materials transparent in 400-1200 nm wavelength. Optionally, the front shell further comprises an anti-reflective coating, to enhance the transmission (not sure you used to enhance the brightness of LED or to received more image by the camera) to improve the image quality by reducing the level of noise.

Similarly, the rear shell also requires a sphere surface to help the capsule navigate through the gastrointestinal tract of a patient. However, because OBM (OBLIQUE BACK ILLUMINATION MICROSCOPY) uses light sources at different wavelengths, and in order to reduce the background noise due to the position of LEDs a flat surface is provided. Therefore the sphere shaped rear end is truncated to provide a flat face for OBM (OBLIQUE BACK ILLUMINATION MICROSCOPY) detection. Additionally, the flat face of the rear shell is made of light transparent materials. Optionally, the flat surface of the rear shell further comprises a variety of coatings, including but not limited to anti-reflective coatings.

The middle shell of the capsule endoscope is substantially cylindrical shaped. The permanent magnetic dipole is placed in the middle shell closer to the end of the front shell, so that the weight center and magnetic center is close. In one example, the weight center and magnetic center is less than 2 mm to offer stable anchor under an external magnetic field. In a preferred example, the weight center and magnetic center is less than 1 mm.

The front shell diameter is the same as the capsule diameter, for example 12 mm. The rear shell have the truncated hemi-sphere with the diameter is 8 mm, for example.

The battery and the magnet are the heavier parts than others in the capsule endoscopy, therefore it is preferred to fix these three parts in the approximate middle of the capsule.

The lens and LEDs of the OBM end should closely attach to the rear shell flat surface to avoid the stray of light. There is an oblique ring in the rear shell to further prevent the stray light.

FIGS. 8-12 illustrates the basic method steps that how the capsule endoscope having one photographic camera and one OBM (OBLIQUE BACK ILLUMINATION MICROSCOPY) camera travels in the gastrointestinal track. In one embodiment, the method comprises providing a capsule endoscope having a permanent magnetic dipole placed in a target area, comprising a liquid/gas interface; and position an external magnetic ball in close proximity to the capsule endoscope so that the magnetic dipole inside the capsule endoscope can changes its position and orientation in response to the movement and rotation of the external magnetic ball. Next, suspending the capsule endoscope either at the liquid/gas interface or in the liquid by applying magnetic field force to the capsule endoscope to balance the weight and floating force experience by the capsule. Preferably, the capsule is suspended horizontally at the liquid/gas interface, having the front end facing the direction of movement. Then the capsule endoscope can move forward and backward along the horizontal direction because of the lateral movement of the external magnet.

Once the capsule endoscope, while being horizontally suspended, is guided into a target area of interest, the capsule endoscope will be reoriented to change its pasture in order for the photographic camera to scan the interior surface and take pictures. The method comprise the steps of flipping the capsule from its horizontal position, and having the front camera pointing towards the area of interest, and identify a marker in the interior area to label its first position; changing its orientation and taking pictures as the capsule rotates in accordance with the rotation and vertical movement of the external magnet.

Figure 8:
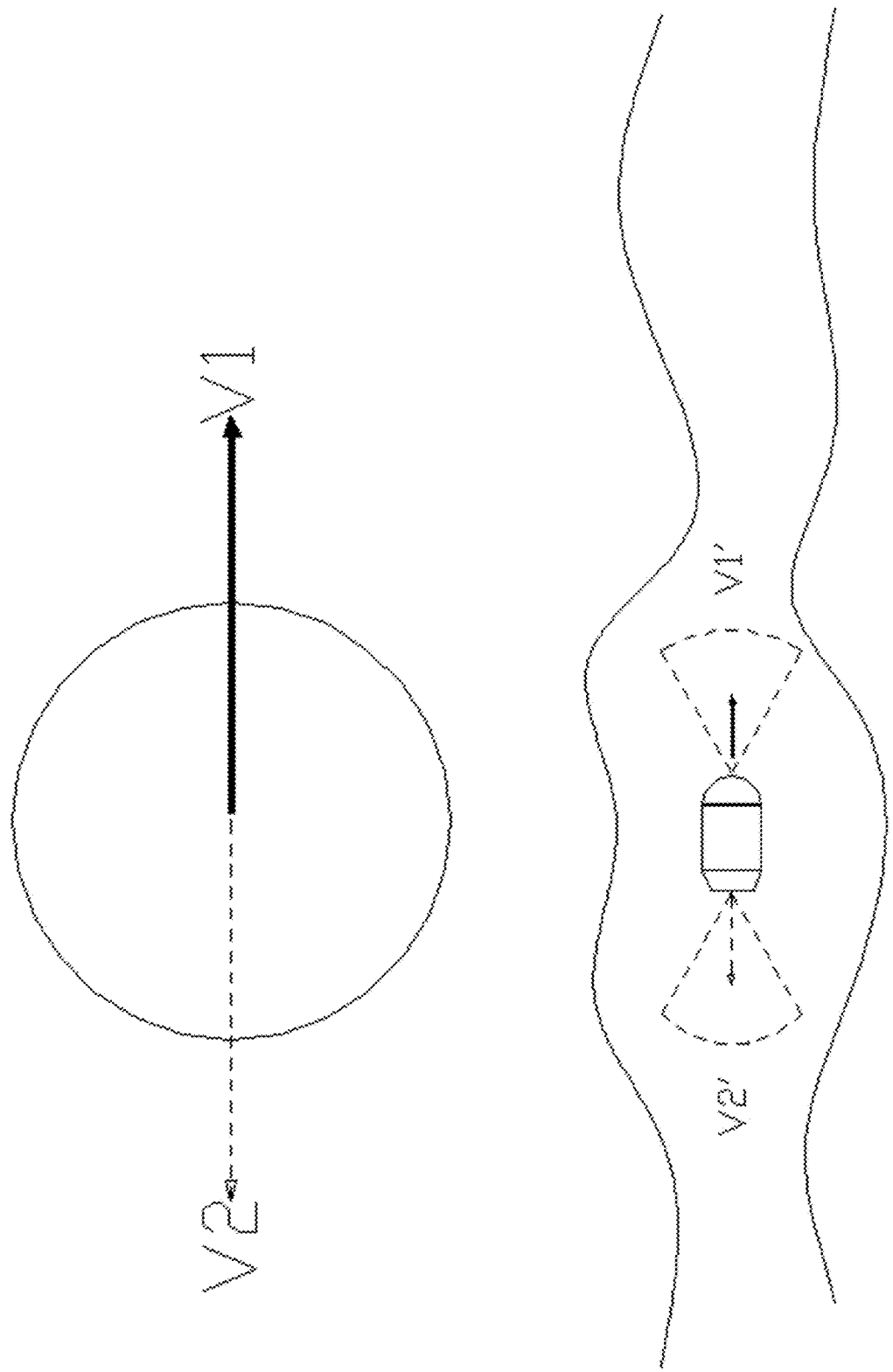
FIG. 8 shows a schematic illustration of an exemplary capsule endoscope in a floating state, wherein the capsule is suspended horizontally and said capsule can be moved forward and backward in accordance with the movement of the external magnetic ball.
Figure 9:
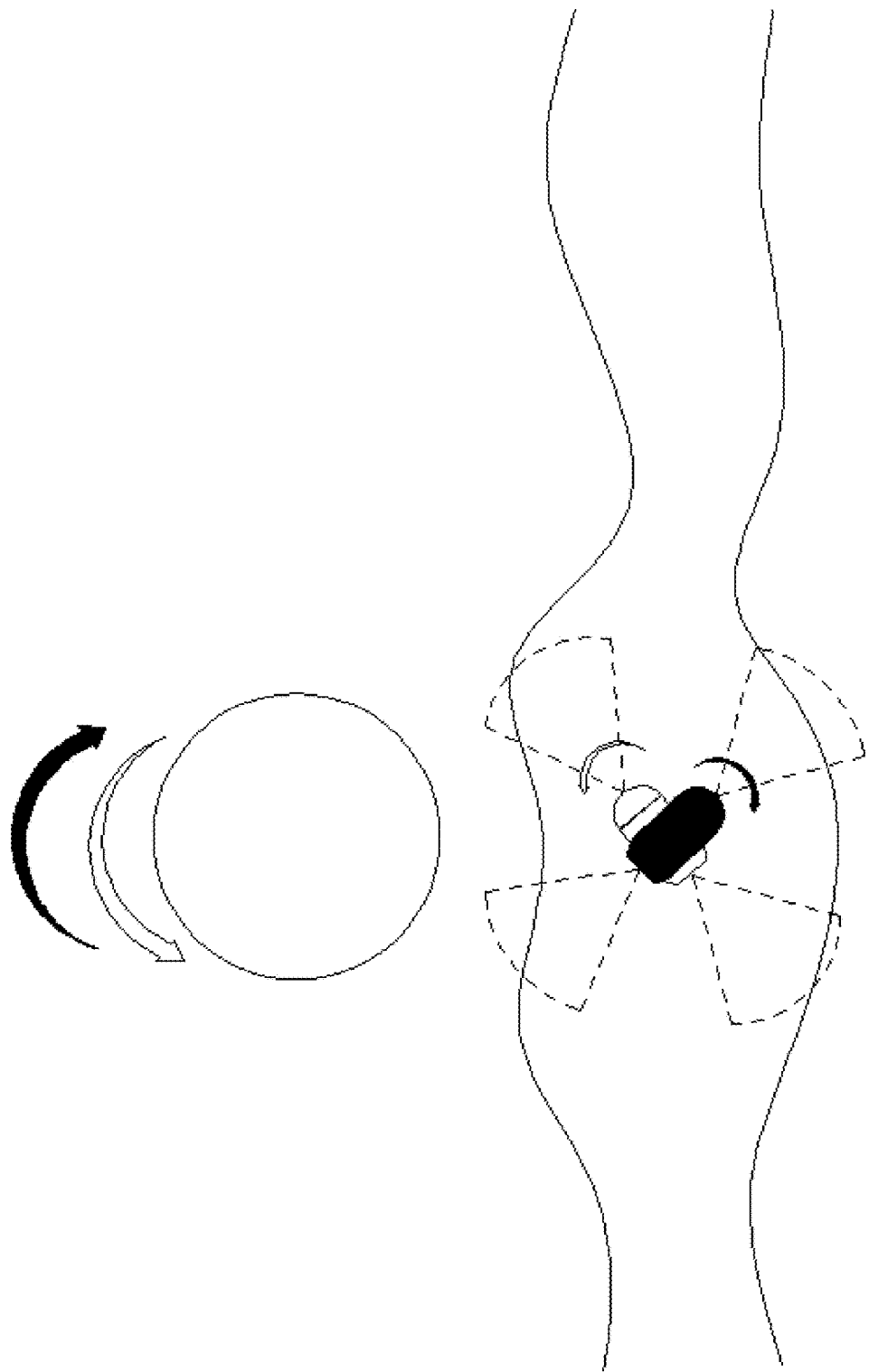
FIG. 9 shows a schematic illustration of an exemplary capsule endoscope floated in a liquid, wherein the capsule is suspended horizontally and said the angle between the capsule and liquid can be adjusted in accordance with the rotational movement of the external magnetic ball.
Figure 10:
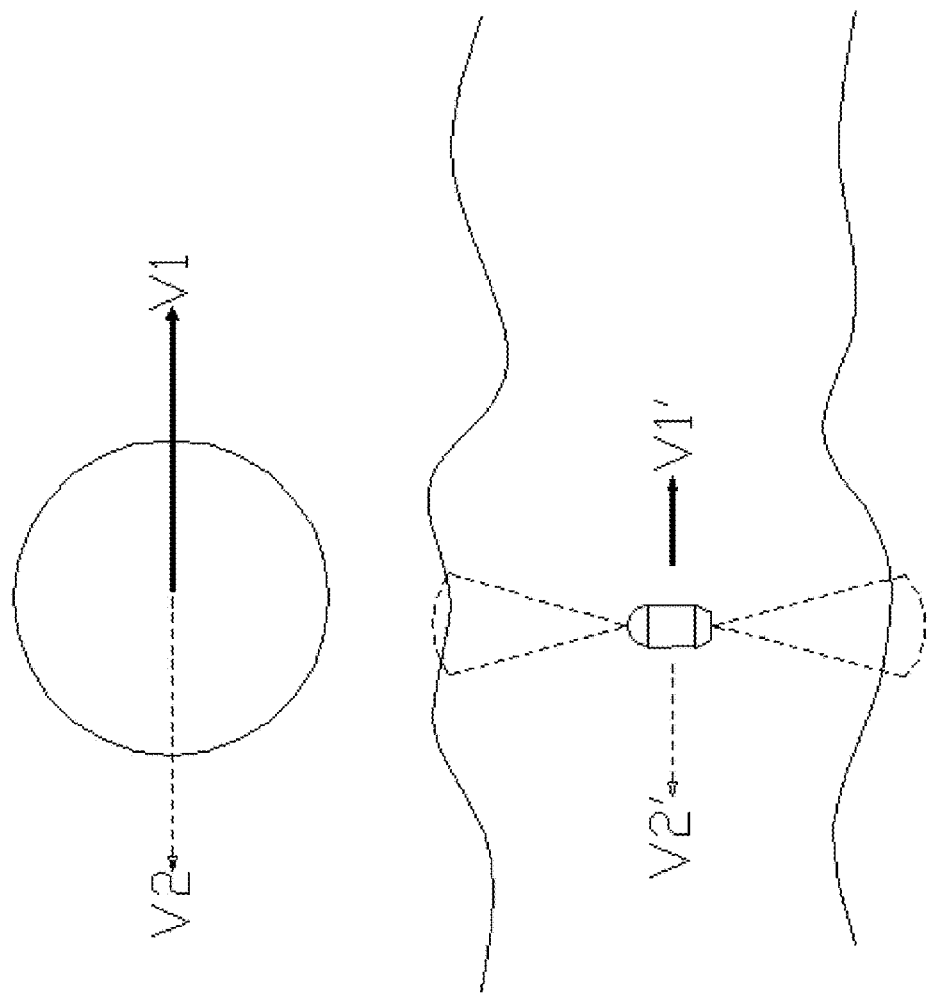
FIG. 10 shows a schematic illustration of an exemplary capsule endoscope in a floating state, wherein the capsule is suspended vertically and said capsule can be moved forward and backward in accordance with the movement of the external magnetic ball.

FIG. 10 schematically illustrates an alternative embodiment of FIG. 8. In another embodiment, the method to navigate the capsule endoscope having one photographic camera and one diagnostic imaging means, comprises providing a capsule endoscope having a permanent magnetic dipole placed in a target area, comprising a liquid/gas interface; and positioning an external magnetic ball in close proximity to the capsule endoscope so that the magnetic dipole inside the capsule endoscope can change its position and orientation in response to the movement and rotation of the external magnetic ball. Next, suspending the capsule endoscope at the liquid/gas interface by applying magnetic field force to the capsule endoscope by balancing the weight and floating force experience by the capsule, wherein the capsule is suspended vertically at the liquid/gas interface. Then moving the capsule endoscope to the left or right direction by the lateral movement of the external magnet, wherein the left and right direction is not parallel to but perpendicular to the length direction of the capsule endoscope, and the left and right direction movement of the capsule endoscope allows the front end of the capsule endoscope facing an exposed interior wall of the target area. Further the photographic camera takes pictures when the capsule endoscope travels laterally along the liquid/gas interface.

FIG. 10 describes a method of scanning the interior surface of the target area by moving the capsules endoscope. Alternatively, scanning an interior surface of the target area can also be performed by anchoring the capsule at a desired position and scan the surface above it by changing its orientation. When the capsule endoscope disclosed in the present invention vertically suspended at the gas/liquid interface, having the front shell positioned above the gas/liquid interface, the capsule can either swing from left to right to scan a slice of the surface above it, or evolve around its anchor position to scan a broader surface of the interior surface. In one embodiment of the present invention, the method to navigate the capsule endoscope having one photographic camera and one diagnostic imaging means, comprises providing a capsule endoscope having a permanent magnetic dipole placed in a target area, comprising a liquid/gas interface; and positioning an external magnetic ball in close proximity to the capsule endoscope so that the magnetic dipole inside the capsule endoscope can change its position and orientation in response to the movement and rotation of the external magnetic ball. Next, suspending the capsule endoscope at a first position at the liquid/gas interface and forming a first tilt angle between the length of the capsule endoscope and gas/liquid interface by applying magnetic field force to the capsule endoscope; rotating the capsule endoscope to either left and right, changing its title angle formed between its length and the gas/liquid interface while being anchored at the first position at the gas/liquid interface, and taking images by the photographic camera by the front end of the capsule endoscope.

Figure 12:
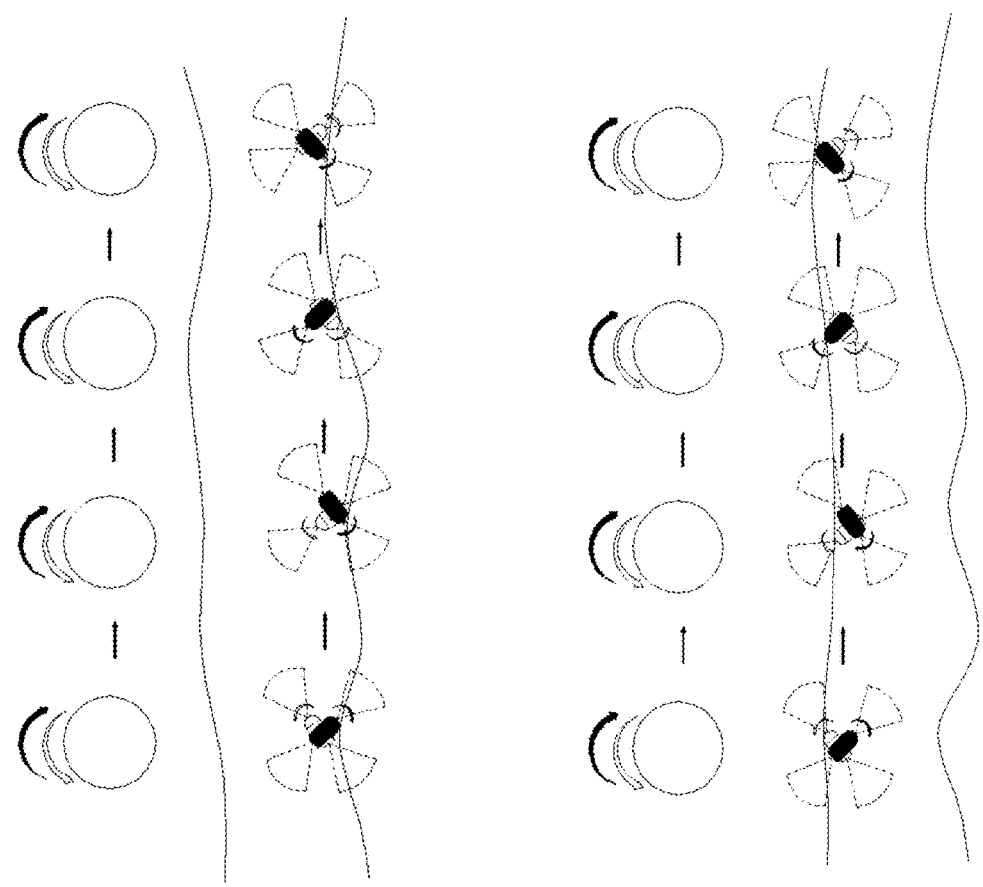
FIG. 12 shows a schematic illustration of an exemplary capsule endoscope located on the wall of colon, wherein the capsule can rotate continuously to scan the interior of the target area.

FIG. 12, illustrated that the capsule can scroll continuously while moving forward in a linear manner, under the influence of the external magnetic field. The capsule can flip when it at the top or bottom.

Figure 11:
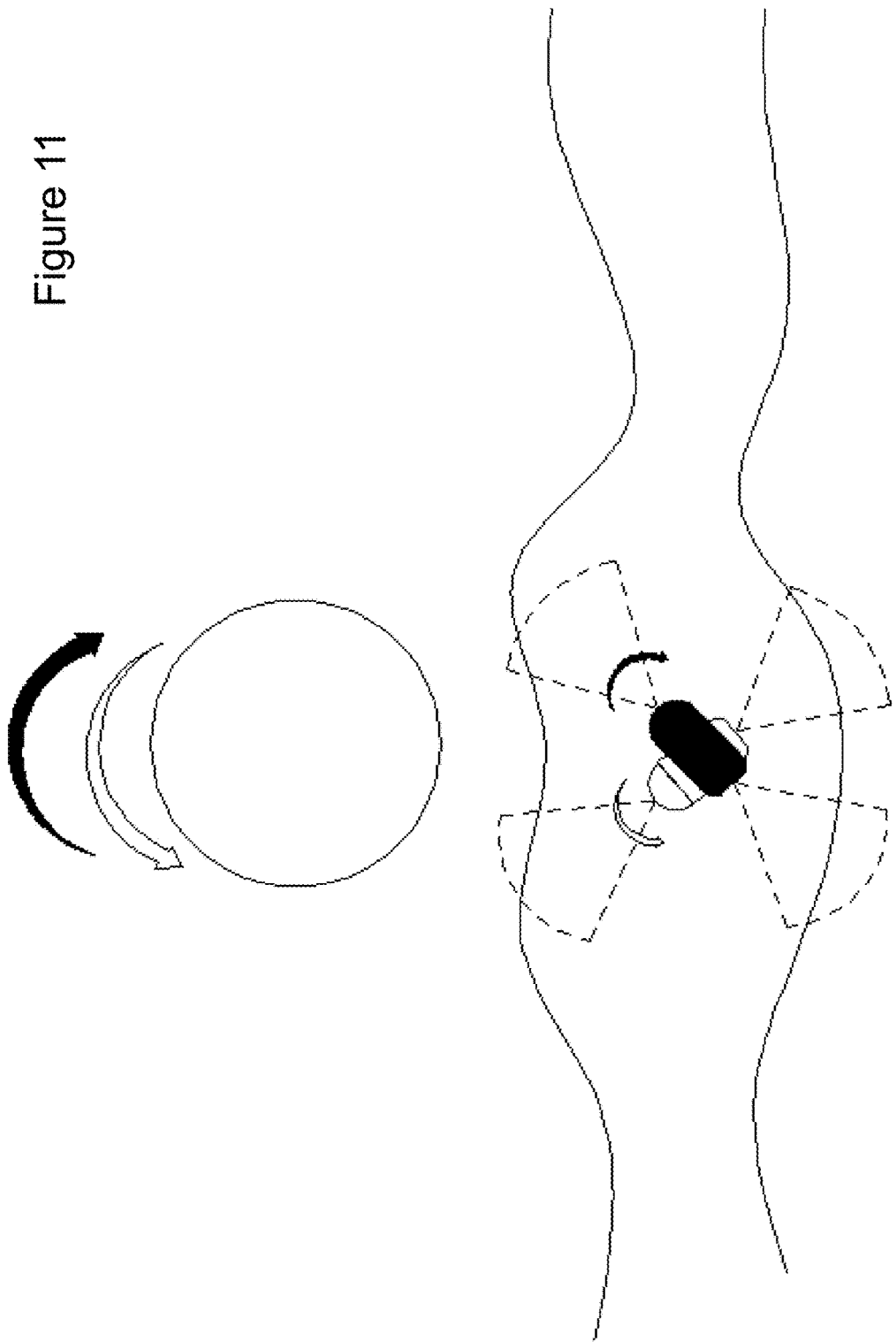
FIG. 11 shows a schematic illustration of an exemplary capsule endoscope floated in a liquid, wherein the capsule is suspended vertically and the angle between the capsule and liquid can be adjusted in accordance with the rotational movement of the external magnetic ball.

Referring to FIGS. 10, 11, 13a and 13b, when the capsule endoscope is introduced into a target area, the capsule is suspended in a way that the front end bearing the photographic camera is above the gas/liquid interface. The photographic camera can take a first picture and rotate from left to right as shown in FIG. 11 or moving up or down with respect to the gas/liquid interface to the interior surface as desired by moving the external magnetic ball vertically or adjusting the vertical distance between the external magnetic and capsule endoscope. Optionally, under some usual circumstances, it is desired to immerse the front end of the capsule endoscope to be underneath the liquid/gas interface. Similarly, the capsule endoscope can moves up and down in accordance with the vertical movement of the external magnet.

FIGS. 8-12, describes when a capsule endoscope is introduce into a target area filled with a gas and liquid, and capsule is navigated in the target area while being suspended. FIGS. 13a-17 describe when a capsule endoscope is introduced into a target area, wherein the target area has been previously vacated and filled with a gas, for example air.

Figure 13B:
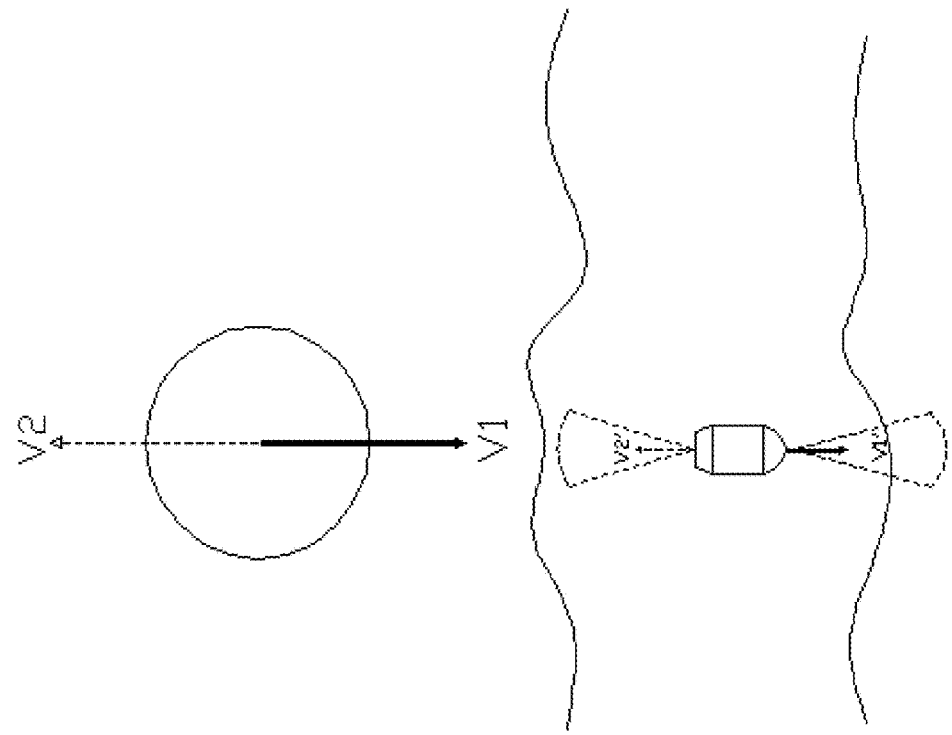
FIG. 13b shows a schematic illustration of an exemplary capsule endoscope floated in a liquid, wherein the capsule's rear end faces towards the magnetic ball and the capsule can move up and down vertically in response to the movement of the external magnetic ball.
Figure 13A:
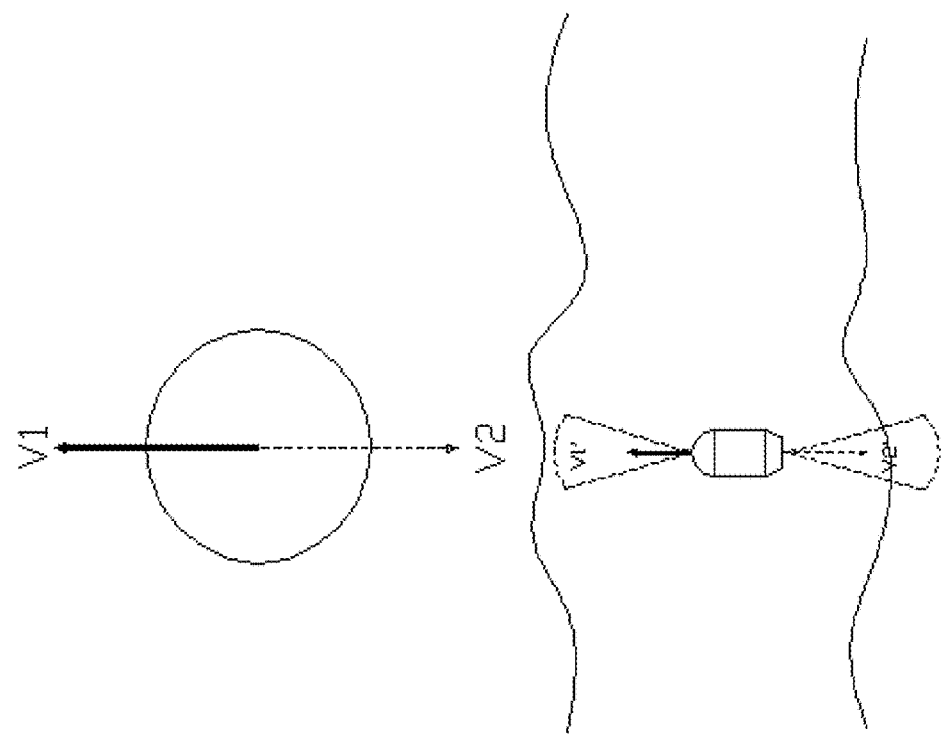
FIG. 13a shows a schematic illustration of an exemplary capsule endoscope floated in a liquid, wherein the capsule's front end faces towards the magnetic ball and the capsule can move up and down vertically in response to the movement of the external magnetic ball.

Referring to FIGS. 13a and 13b, and FIGS. 14a and 14b. when the capsule is introduced into a target area filled with air, the capsule can either be suspended in the air (FIGS. 13a and b) or be placed next to a surface of the interior wall of the target area (FIGS. 14a and b). As illustrated in FIGS. 13a and 13b, the capsule endoscope will adopt an upright position with respect to either a first or second surface, having the front end facing either a first or second surface of the capsule endoscope. Then the capsule can be moved either closer or farther away towards the first or second surface, while the photographic camera can take pictures simultaneously. In one embodiment of the present invention, the method to place the capsule endoscope having one photographic camera and one diagnostic imaging means, comprises providing a capsule endoscope having a permanent magnetic dipole placed in a target area filled with a gas; and positioning an external magnetic ball in close proximity to the capsule endoscope so that the magnetic dipole inside the capsule endoscope can change its position and orientation in response to the movement and rotation of the external magnetic ball. Next, applying magnetic field force to the capsule endoscope to suspend the capsule endoscope at a upright position with respect to a first surface of the target area, having the front end bearing the photographic camera pointing toward the first surface; repositioning the capsule endoscope to be either closer and father away from the first surface and taking images by the photographic camera simultaneously by adjusting the distance between the external magnetic ball and the first surface of the target area.

As illustrated in FIGS. 14*a* and 14*b*, the capsule endoscope is placed in direct contact on a surface of the target area, which is filled with a gas, having the front end facing either a first or second surface of the capsule endoscope. Then the capsule can be moved forward or backward along the first or second surface by moving the external magnetic field along the direction of the first or second surface, while the photographic camera can take pictures simultaneously.

Figure 15:
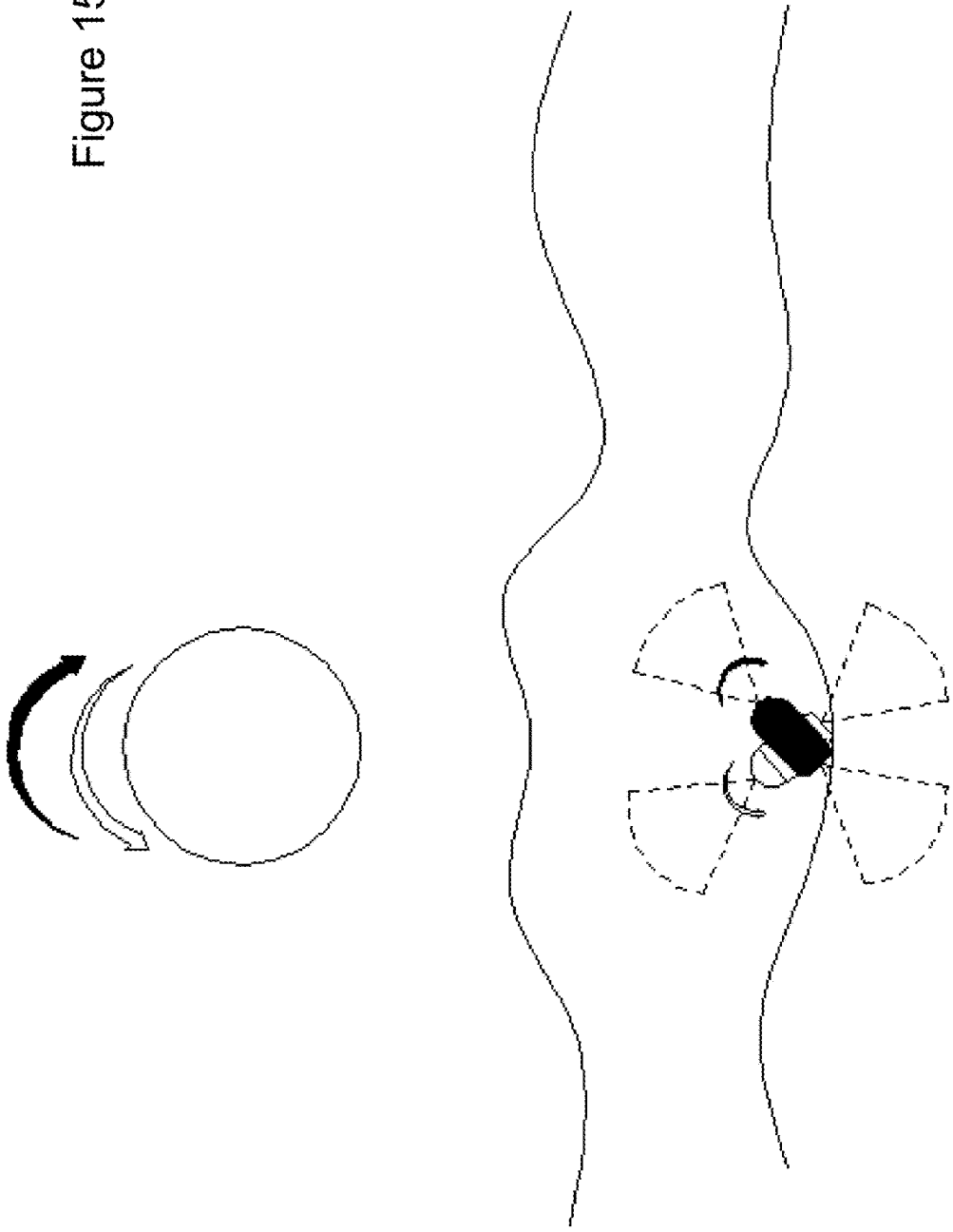
FIG. 15 shows a schematic illustration of an exemplary capsule endoscope in a target area, wherein the capsule endoscope of FIG. 1 can move along the first surface of the target area, capsule endoscope forming a tilt angle with the first surface and capsule scan the second surface.
Figure 16:
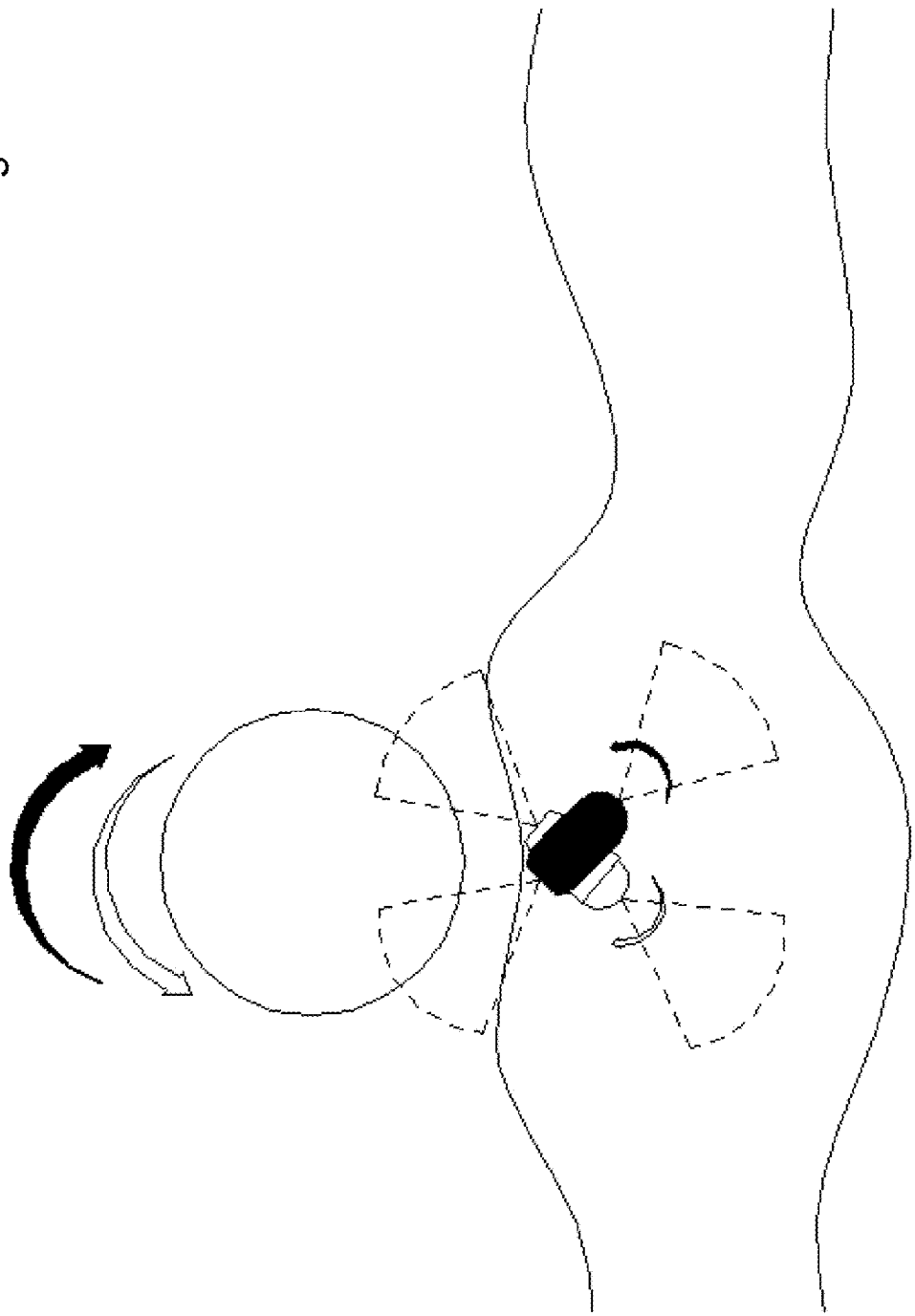
FIG. 16 shows a schematic illustration of an exemplary capsule endoscope in a target area, wherein the capsule endoscope of FIG. 1 can move along the second surface of the target area, capsule endoscope forming a title angle with the second surface and capsule scan the first surface, wherein and second surface is closer to the external magnetic ball than the first surface.
Figure 17:
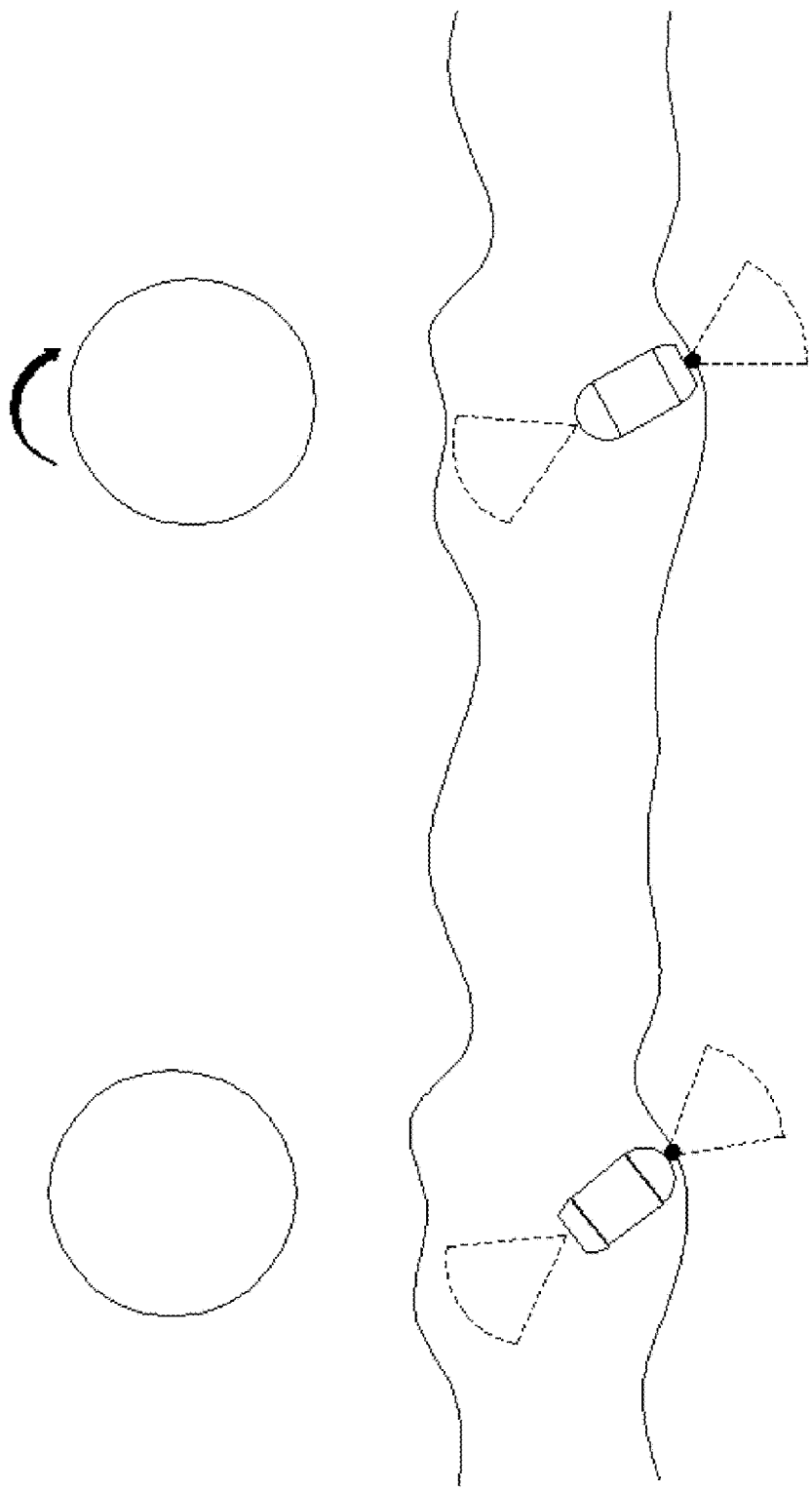
FIG. 17 shows a schematic illustration of an exemplary capsule endoscope in a target area, wherein the capsule endoscope changes its orientation from having the camera pointing to the diseased area to having the OBM (OBLIQUE BACK ILLUMINATION MICROSCOPY) means pointing to the camera.

While as the capsule endoscope moves along a first surface, the front end thereof can be further lifted up and rotate to scan the images of the surface opposing to the first surface as shown in FIGS. 15 and 16. As illustrated in FIG. 15, when the capsule endoscope having one photographic camera and one diagnostic imaging means is placed in a target area filled with a gas, for example, air or $CO_2$, the capsule endoscope will automatically rest and by supported by a first surface of the target area with/without the external magnetic field because of the weight of the capsule endoscope. Next, applying rotational and moving magnetic field to the capsule endoscope, the capsule endoscope will lift up its front end up to take pictures. FIG. 16, shows a follow-up method step to examine the opposing surface of the first surface. The capsule endoscope is hang up on a second surface with is opposite to the first surface having the front end pointing downwards and towards to the first surface, scanning the images of the first surface. In one embodiment of the present invention, the method comprising providing the capsule endoscope having a permanent magnetic dipole; guiding the capsule endoscope into a target area filled with a gas by applying external magnetic field and placing the capsule endoscope as rested on a first surface; lifting the front end of the capsule endoscope up towards a second surface and scanning the second surface by applying rotational magnetic field and taking pictures of the second surface by the photographic camera of housed in the front end of the capsule endoscope. Then dislocating the capsule endoscope from the first surface and moving the capsule endoscope to the surface, hang it upside down while the front end facing toward the first surface by moving the external magnetic ball closer to the second surface, and scanning the surface of the first surface.

In accordance with the aspects of the present invention, the capsule endoscope having both the photographic camera for scanning and a diagnostic imaging means for biopsy, is always using the photographic camera to collect picture data first to decide there is a diseased region which needs further examination. Once the diseased region is determined, the capsule endoscope can be flipped or rotated 180 degrees, to have the diagnostic imaging means facing towards the diseased region and performing an optical biopsy.

FIGS. 8-17 listed fundamental method steps in using the capsule endoscope having both a photographic camera and a diagnostic imaging means. Each method steps as illustrated in meant to be used in conjunction with other method steps to be effectively exam and diagnose a target area. In one embodiment of the present invention, the diagnostic imaging means is OBM (OBLIQUE BACK ILLUMINATION MICROSCOPY). In another embodiment of the present invention, the diagnostic imaging means is Spectrally-encoded confocal microscopy (SECM).

In one embodiment of the present invention, the capsule endoscope comprises a first light source for the photographic camera at the front end, a second light source and a third light source for diagnostic imaging means at the rear end of the capsule endoscope. Where in the first light source can be one or more LEDs and the first and second light source must be able to illuminate the target area at different and distinguishable wavelengths of lights. In one example the first light source includes to two white LEDs, which are identical and produces lights in the visible light region. In another example, the second and third light source is six LEDs, surrounding the camera of the dialogistic the imaging means. In one instance, three of the LEDs are identical and emitting light at a first wavelength, and three of the LEDs are identical and emitting light at a second wavelength, and the first and second wavelength are different and distinguishable. In another instance, the first three LEDs are red emitting LEDs and other three LEDs are blue LEDs. In another example, once a diseased region is determined, the LEDs are configured for illumination of the diseased region by the second and third light sources with orthogonally polarized light.

In one embodiment, the first and second light sources are capable of providing illumination at a range of wavelengths comprising from 0.2 to 300 µm.

In another embodiment, the light source of the first and second light source are selected from a light-emitting diode (LED), a laser, a supercontinuum light source, or a superluminescent diode (SLED).

Figure 18:
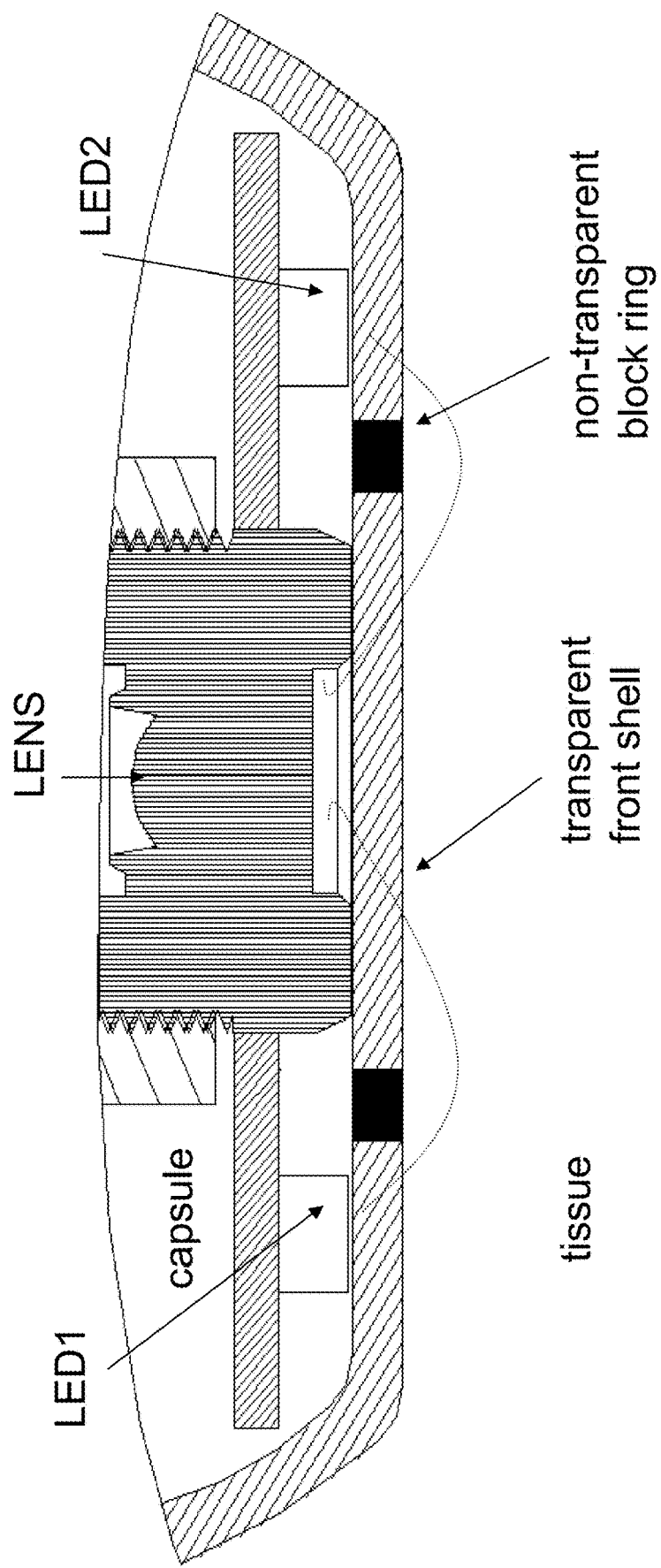
FIG. 18 shows a cross sectional view of the truncated hemisphere end of the capsule endoscope.

In further embodiment of the present invention, referring to FIG. 18, the capsule further comprises a transparent surface and a non-transparent surface, wherein any non-transparent surface is placed in between transparent surfaces. Further the non-transparent surface is placed between the surface next to the LED and the surface next to the OBM lens. The non-transparent surface is placed to prevent the LED light from received by the lens without propagated into the tissue or disease region in the target area (illustrated by the curve arrow shown in FIG. 18).

Figure 19:
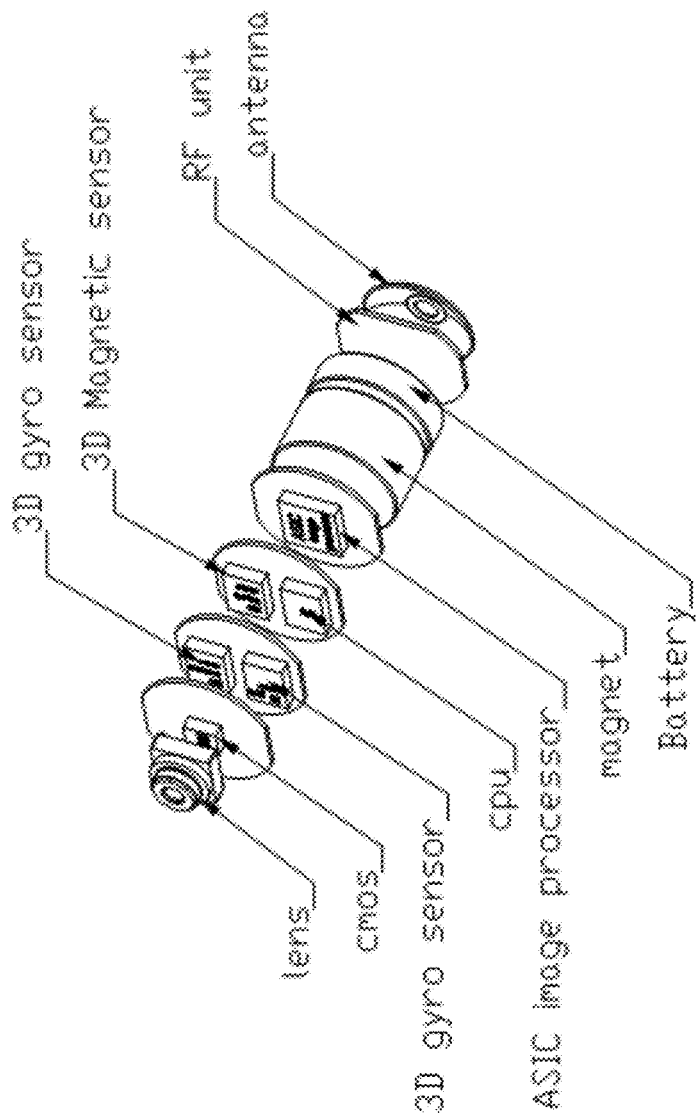
FIG. 19 shows an exploded view of the capsule endoscope.

FIG. 19 further illustrate other components that are desired to be included in a capsule endoscope. For example, including but not limited to a CMOS, 3D magnetic sensor, 3D gyro sensor, CPU and ASIC image processor and a battery.

Figure 20:
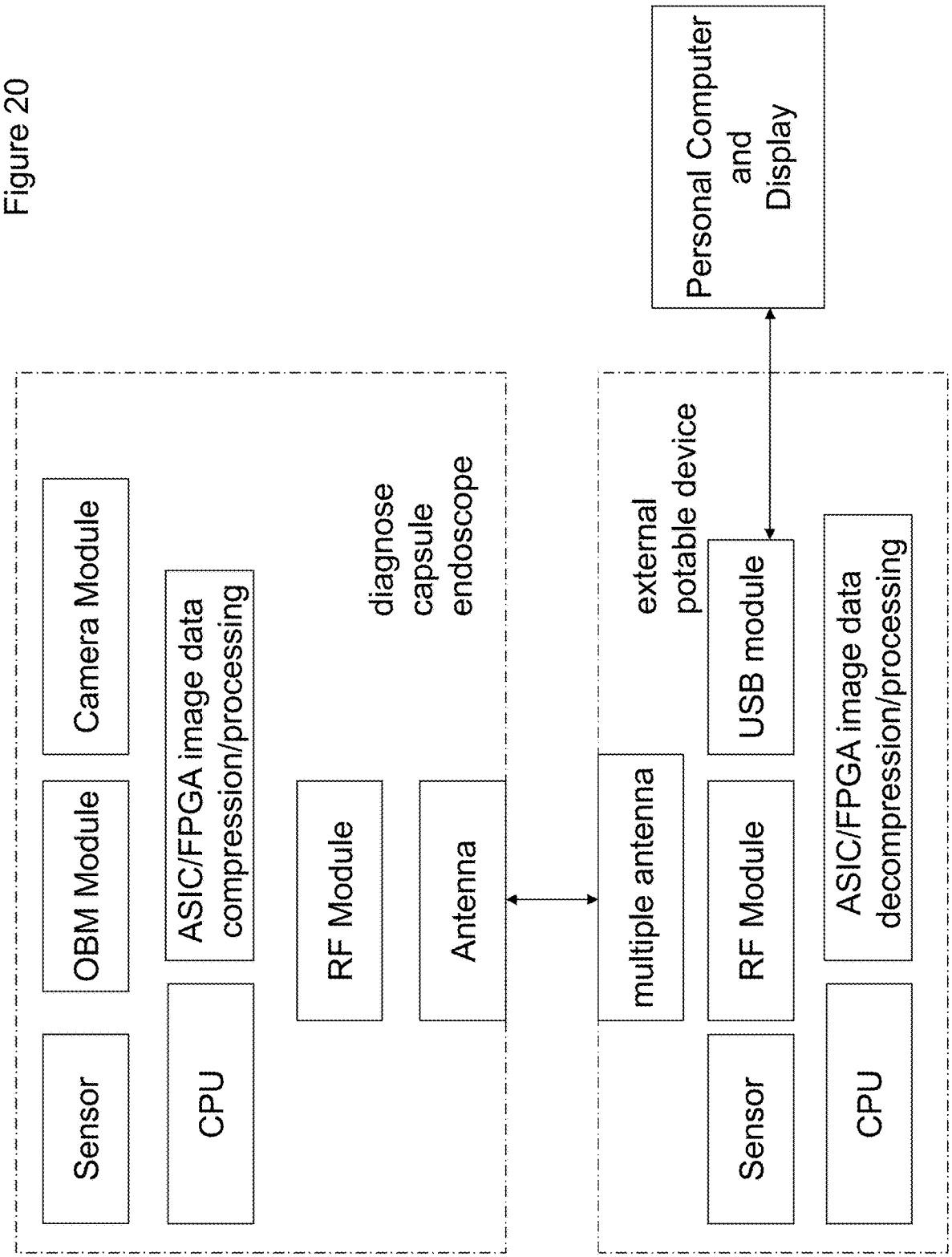
FIG. 20 illustrates an exemplary method steps used in the capsule endoscope examination.

FIG. 20 illustrates the working procedure of the whole imaging system. After the capsule endoscope turns on, all the functions of photographic/video camera and the OBM microscopyic camera can be individually controlled by the CPU and/or ASIC/FPGA inside the capsule. The images obtained by the camera module or OBM module are processed by the ASIC/FPGA module, the timing of taking the images is controlled by CPU. The CPU can read the values of sensors and all those information can be used to calculate the capsule special location, wherein the sensors include all sensors in FIG. 19. The capsule functions can be controlled by the commands that received from the RF module inside the capsule. The RF signal can be either 2.4 GHz or 433 Mhz or other frequencies. The external portable device is used to communicate with the capsule endoscope, receiving imaging and sensor data as well as sending commands to the capsule endoscope. The external portable device can also communicate with PC, PAD or smart phone by USB, Ethernet, Bluetooth, WiFi or other ways to display the image on the screen in real-time. A method of creating a phase contrast image, disclosed herein, comprises preparing a patient's stomach empty and ready for examination;

placing a capsule having a permanent magnetic dipole in situ in the patient, positioning the capsule to a target area;

illuminating the target area of a sample with a first light source to provide a photographic image;

rotating the capsule endoscope for 180 degrees so that the first light source points away from the sample when the same is decided to be a GI pathology;

illuminating the target area of a sample with a second light source and a third light source to provide a oblique back illumination of the target region of the sample and detecting a phase contrast image from light originating from the second and third light source and back illuminating the target region of the sample.

The method further comprises forming a direct contact between the capsule endoscope and the sample by using the external magnetic force to obtain an OBM image.

Further, the step of illuminating the target area of a sample with a first light source to provide a photographic image, further comprises scanning fundus of the patient to check both a ceiling and bottom wall thereof, then scanning the cardiac;

scanning multiple regions of the patient's GI track including a pylorus, and scanning tantrum.

The aforementioned embodiments describe the system and method for an endoscopic imaging apparatus comprising a wireless capsule endoscope, wherein one photographic camera is on one end and the diagnostic imagining means is on the other end. In accordance with another aspects of the present invention, the endoscopic imaging apparatus can also comprise a tethered capsule endoscope having both the photographic camera and the diagnostic imaging means on the front end, as the embodiments listed below.

The invention claimed is:

1. An endoscopic imaging apparatus, comprising:
an ingestible endoscopy capsule comprising
a permanent magnetic dipole and having a cylindrical housing and a hemi one hemi-spherical end and truncated hemi-spherical end, configured to form a direct contact with a sample,
wherein the capsule length is in parallel to the direction of the magnetic dipole;
a first light source for photography or video;
an external positioning and orientation system
to position and/or orientate the capsule in a target area including at least one magnet for positioning and/or orientating the endoscopy capsule within a patient, and
one diagnostic imaging means,
which is oblique back illumination microscopy (OBM), configured to perform an imaging having a depth resolution of 1-30 μm and comprises a second light source,
wherein the diagnostic imaging means comprises an optical conduit to communicate light in at least one direction selected from toward the sample and away from the sample,
wherein lens of OBM adheres to an inner surface of the truncated hemi-spherical end;
the truncated hemi-spherical end comprises a plurality of transparent surfaces and a plurality of non-transparent surfaces;
each non-transparent surface is placed in between the plurality of transparent surfaces;
each non-transparent surface is placed between the surface next to the second light source and the surface adhere to the lens of OBM, configured to prevent light from the second light source received by the lens of OBM without propagated into the sample.

2. The endoscopic imaging apparatus of claim 1, wherein the capsule is less than 30 mm in a first dimension.

3. The endoscopic imaging apparatus of claim 1, wherein the capsule is less than 10 mm in a second dimension.

4. The endoscopic imaging apparatus of claim 1, wherein the capsule weighs greater than 3 g.

5. The endoscopic imaging apparatus of claim 1, wherein the capsule further comprises a three-dimension magnetic sensor.

6. The endoscopic imaging apparatus of claim 1, wherein the capsule further comprises a three-dimension gravity sensor.

7. The endoscopic imaging apparatus of claim 1, wherein the diagnostic imaging means comprises a third light source.

8. The endoscopic imaging apparatus of claim 1 further comprises four to six LEDs.

9. The endoscopic imaging apparatus of claim 7, configured for illumination of the target area by the second and third light sources with light of different distinguishable wavelengths.

10. The endoscopic imaging apparatus of claim 7, configured for illumination of the sample by the second and third light sources with orthogonally polarized light.

11. The endoscopic imaging apparatus of claim 7, wherein the first and second light sources are capable of providing illumination at a range of wavelengths comprising from 0.2 to 300 μm.

12. The endoscopic imaging apparatus of claim 7, wherein the first and second light sources are selected from a light-emitting diode (LED), a laser, a supercontinuum light source, or a superluminescent diode (SLED).

13. The endoscopic imaging apparatus of claim 7, wherein the diagnostic imaging means comprises a photo detector array and the photo detector array is a charge coupled device (CCD) or a CMOS (complementary metal oxide semiconductor) camera sensor.

14. The endoscopic imaging apparatus of claim 7, wherein the diagnostic imaging means, configured so that the axis of illumination of the sample with the first light source and the axis of detection of light originating from the first light source are displaceable by from about 0.2 mm to about 5 mm.

15. The endoscopic imaging apparatus of claim 7, wherein the first light source is on the opposite side of the second light source.

16. The endoscopic imaging apparatus of claim 7, wherein the third light and second light source are on the same side of the capsule.

17. A method of creating a phase contrast image using the capsule in claim 1, comprising:
preparing a target area patient's stomach empty and ready for examination;
placing a capsule having a permanent magnetic dipole in situ in the patient,
positioning the capsule of claim 1 to a target area;
illuminating the target area of a sample with a first light source to provide a photographic image;
rotating the capsule endoscope for 180 degrees so that the first light source points away from the sample;

illuminating the target area of a sample with a second light source and a third light source to provide an oblique back illumination of the target region of the sample and detecting a phase contrast image from light originating from the second and third light source and back illuminating the target region of the sample.

18. The method of claim 17 further comprises forming a direct contact between the capsule endoscope and the sample by using the external magnetic force to obtain an OBM image.

* * * * *